United States Patent [19]
Uda et al.

[11] Patent Number: 5,840,881
[45] Date of Patent: Nov. 24, 1998

[54] COMPOSITION CONTAINING A WATER-INSOLUBLE OR SLIGHTLY WATER-SOLUBLE COMPOUND WITH ENHANCED WATER-SOLUBILITY

[75] Inventors: Yoshiaki Uda, Yonago; Takako Yamauchi, Takarazuka; Yasushi Nakagawa, Kawanishi; Toshihiro Ishiguro, Toyono-gun; Masahide Oka, Kawanishi; Takamasa Yamaguchi, Kobe; Ikuo Nogami, Nagaokakyo, all of Japan

[73] Assignee: Takeda Chemical Industries, Ltd., Osaka, Japan

[21] Appl. No.: 437,227

[22] Filed: May 8, 1995

Related U.S. Application Data

[63] Continuation-in-part of Ser. No. 353,326, Dec. 5, 1994, abandoned, and Ser. No. 152,122, Nov. 15, 1993, Pat. No. 5,434,061.

[30] Foreign Application Priority Data

| | | | |
|---|---|---|---|
| Nov. 27, 1992 | [JP] | Japan | 6-318807 |
| Mar. 11, 1993 | [JP] | Japan | 5-050652 |
| Jul. 13, 1993 | [JP] | Japan | 5-173121 |
| Dec. 6, 1993 | [JP] | Japan | 5-305597 |

[51] Int. Cl.$^6$ ............................ C08B 37/16
[52] U.S. Cl. ............ 536/46; 536/4.1; 536/103; 536/122; 127/32; 527/300; 527/310; 527/311; 527/312; 514/58
[58] Field of Search ............ 536/4.1, 32, 46, 536/103, 122; 127/32; 527/300, 310, 311, 312; 514/58

[56] References Cited

U.S. PATENT DOCUMENTS 5,241,059  8/1993  Yoshinaga.

FOREIGN PATENT DOCUMENTS

| | | |
|---|---|---|
| 0 312 352 | 4/1989 | European Pat. Off. . |
| 0 519 428 | 12/1992 | European Pat. Off. . |
| 0 599 646 | 6/1994 | European Pat. Off. . |
| WO91/04026 | 4/1991 | WIPO . |
| WO91/18022 | 11/1991 | WIPO . |

OTHER PUBLICATIONS

Uekama et al., Journal of Controlled Release, vol. 25. No. 1/02, 27 May 1993 pp. 99–106.

*Primary Examiner*—James O. Wilson
*Attorney, Agent, or Firm*—Wenderoth, Lind & Ponack, L.L.P.

[57] ABSTRACT

A composition is disclosed comprising a water-insoluble or slightly water-soluble compound and a branched cyclodextrin-carboxylic acid. The branched cyclodextrin-carboxylic acid significantly increases the water-solubility of the compound. Also disclosed is a method of enhancing water-solubility of the compound.

6 Claims, 6 Drawing Sheets

it does.

COMPOSITION CONTAINING A WATER-INSOLUBLE OR SLIGHTLY WATER-SOLUBLE COMPOUND WITH ENHANCED WATER-SOLUBILITY

REFERENCE TO RELATED APPLICATIONS

This is a continuation-in-part of application Ser. No. 08/353,326 filed Dec. 5, 1994, now abandoned and application Ser. No. 08/152,122 filed Nov. 15, 1993, now U.S. Pat. No. 5,434,061.

FIELD OF THE INVENTION

The present invention relates to a composition containing a water-insoluble or slightly water-soluble compound with enhanced water-solubility. Specifically, it relates to a composition containing a water-insoluble or slightly water-soluble compound useful as medicaments, cosmetics, agricultural chemicals, food and drink, etc; the water solubility of the compound being enhanced by combining it with a branched cyclodextrin-carboxylic acid which is a novel cyclodextrin derivative.

BACKGROUND OF THE INVENTION

It is a most general and important problem in the field of pharmaceutics to enhance the water-solubility of water-insoluble or slightly water-soluble drugs. Cyclodextrins have been used as an effective means to solve this problem. Cyclodextrins have been used as food additives or cosmetic additives, or for providing suitable volatility or improving taste or smell, or for emulsification, powdering or stabilization, as well as for enhancing solubility of medicaments or agricultural chemicals. It is believed that these effects of cyclodextrins are produced by the formation of complexes containing active ingredients of pharmaceutical compositions, etc., in the cyclodextrins.

Various homologs of such cyclodextrins are known. Their water solubilities vary with their kinds. For example, α-, β- and γ-cyclodextrins consist of six, seven and eight glucose units, respectively, that are joined in such a way as to form a ring, and it is reported that the water-solubilities of α-, β- and γ-cyclodextrins are about 15%, about 2% and about 23%, respectively.

Incidentally, to enhance the water-solubility of water-insoluble or slightly water-soluble compounds by using a cyclodextrin, the cyclodextrin per se must have a high water-solubility. However, the water-solubilities of conventionally used cyclodextrins are unsatisfactory.

Cyclodextrins used in medicaments to enhance the water-solubility of water-insoluble or slightly water-soluble compounds must be highly safe for the human body because they are administered to the human body as injections, etc. Thus, there is a need for cyclodextrins that form suitable complexes with drugs to promote solubilization of the drugs in water and have no harmful effect on the human body.

OBJECTS OF THE INVENTION

A main object of the present invention is to provide a composition containing a water-insoluble or slightly water-soluble compound with enhanced water-solubility.

Another object of the present invention is to provide a method of enhancing solubility in water of a water-soluble or slightly water-soluble compound.

These objects as well as other objects and advantages of the present invention will become apparent to those skilled in the art from the following description with reference to the accompanying drawings.

SUMMARY OF THE INVENTION

The present inventors have intensively studied to enhance the water-solubilities of water-insoluble or slightly water-soluble compounds by using cyclodextrins. As a result, it has been found that use of a novel cyclodextrin having certain improved characteristics can achieve the above objects.

The present invention provides a composition comprising a water-insoluble or slightly water-soluble compound and a branched cyclodextrin-carboxylic acid.

The present invention also provides a method of enhancing solubility in water of a water-insoluble or slightly water-soluble compound, which comprises combining the water-insoluble or slightly water-soluble compound with a branched cyclodextrin-carboxylic acid.

DETAILED DESCRIPTION OF THE INVENTION

Figure 1:
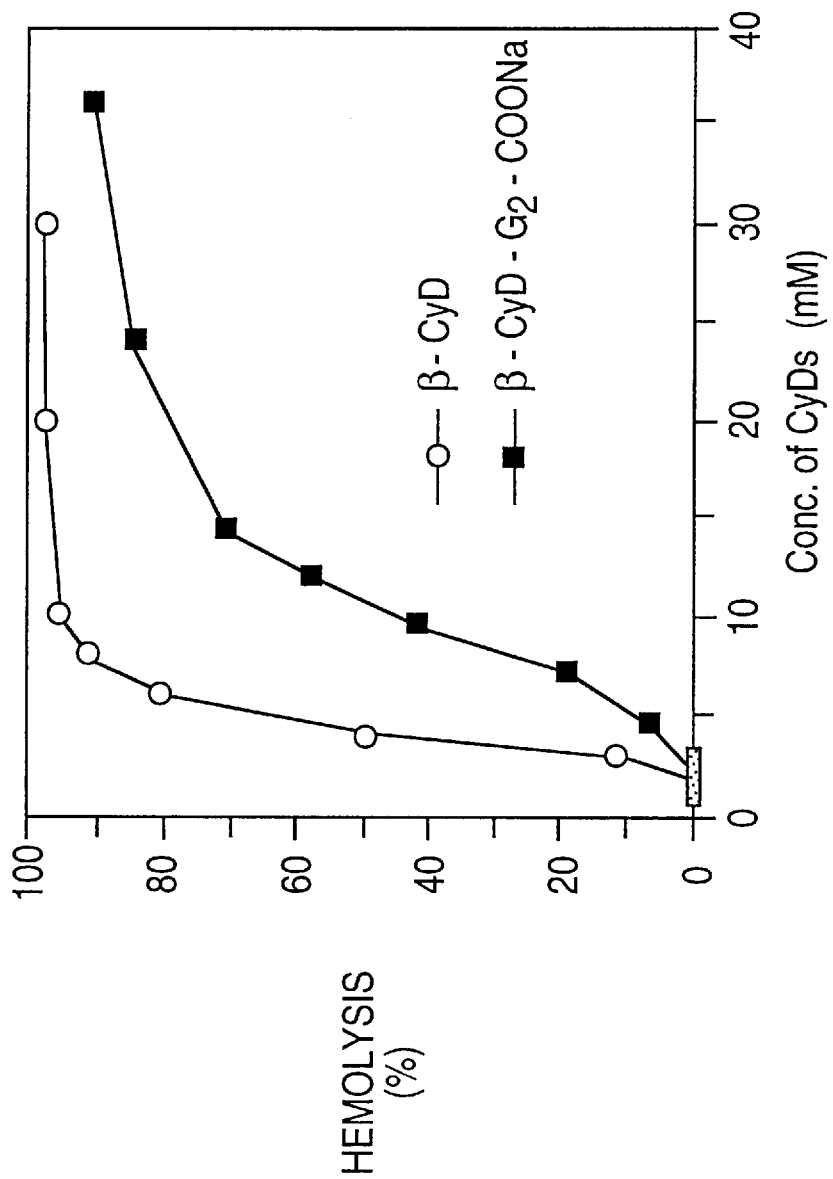
FIG. 1 is a graph showing hemolytic effects of sodium 6-O-cyclomaltoheptaosyl-(6→1)-α-D-glucosyl-(4→1)-O-α-D-glucuronate (β-CyD-$G_2$-COONa) and β-cyclodextrin (β-CyD) on rabbit erythrocytes.

The branched cyclodextrin-carboxylic acid to be used in the present invention is intended to include its free carboxylic acid, and a salt thereof with an alkali metal (e.g., lithium, sodium, potassium, etc.), alkaline earth metal (e.g., calcium, magnesium, etc.), etc. These branched cyclodextrin-carboxylic acids can be used alone or in combination thereof, or as mixtures of their free carboxylic acids and salts thereof.

The branched cyclodextrin-carboxylic acid is a cyclodextrin having an organic group containing at least one carboxyl group at the 6-O-position of at least one glucose unit of the cyclodextrin ring.

The cyclodextrin ring in the branched cyclodextrin-carboxylic acid has, for example, 6, 7 or 8 glucose units. Preferably, the cyclodextrin ring has 7 glucose units. Examples of the cyclodextrin include α-cyclodextrin, β-cyclodextrin and γ-cyclodextrin.

It is preferred that the organic group containing at least one carboxyl group has 1 to 3 glucose units, and that at least one of the hydroxymethyl groups of the glucose units in the organic group is oxidized to a carboxyl group. It is also preferred that the organic group is 2-carboxyethyl or 2-carboxy-2-hydroxyethyl.

Examples of the branched cyclodextrin-carboxylic acid include 6-O-cyclomaltohexaosyl-(6→1)-α-D-glucosyl-(4→1)-O-α-D-glucuronic acid (cyclomaltohexaosyl-(6→1)-O-α-D-glucopyranosyl-(4→1)-O-α-D-glucopyranosiduronic acid) (hereinafter also abbreviated as α-CyD-G$_2$-COOH; the abbreviations of the following compounds are likewise shown in the parentheses), 6-O-cyclomaltoheptaosyl-(6→1)-α-D-glucosyl-(4→1)-O-α-D-glucuronic acid (cyclomaltoheptaosyl-(6→1)-O-α-D-glucopyranosyl-(4→1)-O-α-D-glucopyranosiduronic acid) (β-CyD-G$_2$-COOH), 6-O-cyclomaltooctaosyl-(6→1)-α-D-glucosyl-(4→1)-O-α-D-glucuronic acid (cyclomaltooctaosyl-(6→1)-O-α-D-glucopyranosyl-(4→1)-O-α-D-glucopyranosiduronic acid) (γ-CyD-G$_2$-COOH), 6-O-cyclomaltohexaosyl-(6→1)-α-D-glucuronic acid (cyclomaltohexaosyl-(6→1)-O-α-D-glucopyranosiduronic acid) (β-CyD-G$_1$-COOH), 6-O-cyclomaltoheptaosyl-(6→1)-α-D-glucuronic acid (cyclomaltoheptaosyl-(6→1)-O-α-D-glucopyranosiduronic acid) (β-CyD-G$_1$-COOH), 6-O-cyclomaltooctaosyl-(6→1)-α-D-glucuronic acid (cyclomaltooctaosyl-(6→1)-O-α-D-glucopyranosiduronicacid) (γ-CyD-G$_1$-COOH), 2-O-(6-cyclomaltohexaosyl)-acetic acid (α-CyD-CH$_2$COOH), 2-O-(6-cyclomaltoheptaosyl)-acetic acid (β-CyD-CH$_2$COOH), 2-O-(6-cyclomaltooctaosyl)-acetic acid (γ-CyD-CH$_2$COOH), 3-O-(6-cyclomaltoheptaosyl)-propionic acid (β-CyD-CH$_2$CH$_2$COOH), 2-hydroxy-3-O-(6-cyclomaltoheptaosyl)-propionic acid (3-O-(6-cyclomaltoheptaosyl)-2-hydroxy-propionic acid) (β-CyD-CH$_2$CH(OH)—COOH), 7$^A$,7$^C$-di-O-[α-D-glucuronyl-(1→4)-O-α-D-glucosyl]-(1→6)-maltoheptaose (β-CyD-(G$_2$COOH)$_2$), 6-O-cyclomaltoheptaosyl-O-α-D-maltosyl-(4→1)-O-α-D-glucuronic acid (cyclomaltoheptaosyl-(6→1)-O-α-D-glucopyranosyl-(4→1)-O-α-D-glucopyranosyl-(4→1)-O-α-D-glucopyranosiduronic acid) (β-CyD-G$_3$-COOH), and their salts described above (e.g., sodium salt of β-CyD-G$_2$-COOH (likewise abbreviated as β-CyD-G$_2$-COONa) (sodium cyclomaltoheptaosyl-(6→1)-O-α-D-glucopyranosyl-(4→1)-O-α-D-glucopyranosiduronate)).

Specifically, 6-O-cyclomaltohexaosyl-(6→1)-α-D-glucosyl-(4→1)-O-α-D-glucuronic acid (α-CyD-G$_2$-COOH), 6-O-cyclomaltoheptaosyl-(6→1)-α-D-glucosyl-(4→1)-O-α-D-glucuronic acid (β-CyD-G$_2$-COOH) and 6-O-cyclomaltooctaosyl-(6→1)-α-D-glucosyl-(4→1)-O-α-D-glucuronic acid (γ-CyD-G$_2$-COOH) are novel branched cyclodextrin-carboxylic acids containing α-cyclodextrin (containing 6 glucose units), β-cyclodextrin (containing 7 glucose units) and γ-cyclodextrin (containing 8 glucose units), respectively. In each of these branched cyclodextrin-carboxylic acids, maltose is attached as a branch to one of the glucose units of the cyclodextrin ring through an α-(1→6) linkage, and the hydroxymethyl group (—CH$_2$OH) at the 6-position of the terminal glucose unit of the maltose is oxidized to a carboxyl group to give glucuronic acid.

6-O-Cyclomaltohexaosyl-(6→1)-α-D-glucuronic acid (α-CyD-G$_1$-COOH), 6-O-cyclomaltoheptaosyl-(6→1)-α-D-glucuronic acid (β-CyD-G$_1$-COOH) and 6-O-cyclomaltooctaosyl-(6→1)-α-D-glucuronic acid (γ-CyD-G$_1$-COOH) are novel branched cyclodextrin-carboxylic acids. In each of these branched cyclodextrin-carboxylic acids, glucose is attached as a branch to one of the glucose units of the cyclodextrin ring through an α-(1→6) linkage, and the hydroxymethyl group (—CH$_2$OH) at the 6-position of the glucose is oxidized to a carboxyl group to give glucuronic acid.

Further, each of 2-O-(6-cyclomaltohexaosyl)-acetic acid (α-CyD-CH$_2$COOH), 2-O-(6-cyclomaltoheptaosyl)-acetic acid (β-CyD-CH$_2$COOH) and 2-O-(6-cyclomaltooctaosyl)-acetic acid (γ-CyD-CH$_2$COOH) is a novel branched cyclodextrin-carboxylic acid wherein a carboxymethyl group is attached as a branch to one of the glucose units of the cyclodextrin ring.

These novel branched cyclodextrin-carboxylic acids or salts thereof can be prepared, for example, as follows.

In the case of 6-O-cyclomaltohexaosyl-(6→1)-α-D-glucosyl-(4→1)-O-α-D-glucuronic acid (α-CyD-G$_2$-COOH), 6-O-cyclomaltoheptaosyl-(6→1)-α-D-glucosyl-(4→1)-O-α-D-glucuronic acid (β-CyD-G$_2$-COOH) and 6-O-cyclomaltooctaosyl-(6→1)-α-D-glucosyl-(4→1)-O-α-D-glucuronic acid (γ-CyD-G$_2$-COOH) or salts thereof, firstly, maltosyl-α-cyclodextrin (G$_2$-α-CyD), maltosyl-β-cyclodextrin (G$_2$-β-CyD) and maltosyl-γ-cyclodextrin (G$_2$-γ-CyD) are prepared. These cyclodextrin derivatives can be obtained, for example, by condensing a-cyclodextrin, β-cyclodextrin or γ-cyclodextrin with maltose using isoamylase produced by microorganisms belonging to the genus Pseudomonas (Susumu Hizukuri, Amylase Symposium (1985)). This isoamylase is an enzyme discovered by Harada et al. (Biochim. Biophys. Acta, 212, 458 (1970)) that hydrolyzes α-(1→6) linkages of glycogen or amylopectin to give amylose-like straight chain polysaccharides. The above condensation can be achieved by the reverse reaction of the hydrolysis of isoamylase.

For example, β-cyclodextrin, maltose and isoamylase are reacted in an appropriate buffer at 40° to 65° C. for about 48 hours to give maltosyl-β-cyclodextrin. Maltose and isoamylase are used in amounts of 0.5 to 2 mol and 50,000 to 200,000 U per mol of cyclodextrin, respectively. 1U of isoamylase means the amount of the enzyme that produces reducing power giving 1 μmol of D-glucose per minute (Agric. Biol. Chem., 41, 2077 (1977)). Normally, the reaction mixture is cooled to precipitate excess cyclodextrin, and the precipitated cyclodextrin is removed. Then the residue is purified by column chromatography to give maltosyl-β-cyclodextrin. The cyclodextrin used for preparation of maltosyl-cyclodextrin is not limited to β-cyclodextrin containing 7 glucose units. For example, α-cyclodextrin containing 6 glucose units and γ-cyclodextrin containing 8 glucose units can also be used. The more the number of glucose units, the higher the rate of the reaction between the cyclodextrin and maltose.

Then, the hydroxymethyl group (—CH$_2$OH) in the glucose in the branched part of the branched maltosyl-cyclodextrin thus obtained is oxidized to a carboxyl group to obtain a novel branched cyclodextrin-carboxylic acid. The oxidation is preferably carried out according to the method described in EP-A-0599646 (Japanese Patent Application No. 5-288284) or modifications thereof, for example, by microbiological selective oxidation using microorganisms belonging to the genus Pseudogluconobacter. That is, the preferred method comprises (i) contacting and reacting maltosyl-cyclodextrin with a microorganism belonging to the genus Pseudogluconobacter capable of oxidizing a hydroxylmethyl group in the glucose in the branched part to a carboxyl group or its processed material to oxidize the hydroxymethyl group to a carboxyl group, (ii) producing and accumulating maltosyl-cyclodextrin-carboxylic acid, and (iii) collecting it. The microbial cells or a culture broth thereof can be prepared according to the method described in, for example, U.S. Pat. No. 4,877,735 (JP-A 1-85088) or EP-A-221707.

Any microorganisms belonging to the genus Pseudogluconobacter can be used insofar as they are capable of oxidizing a hydroxymethyl group and/or OH-containing hemiacetal moiety of a saccharide to a carboxyl group. They include mutants thereof obtained by normal mutagenesis procedures such as treatment with a chemical mutagen, for example, nitrosoguanidine, ultraviolet irradiation, etc., or gene recombination, etc. In particular, a microorganism of *Pseudogluconobacter saccharoketogenes* is preferred. Examples thereof include the following microorganisms disclosed in EP-A-221,707.

*Pseudogluconobacter saccharoketogenes* K591s strain: FERM BP-1130, IFO 14464

*Pseudogluconobacter saccharoketogenes* 12-5 strain: FERM BP-1129, IFO 14465

*Pseudogluconobacter saccharoketogenes* TH14-86 strain: FERM BP-1128, IFO 14466

*Pseudogluconobacter saccharoketogenes* 12-15 strain: FERM BP-1132, IFO 14482

*Pseudogluconobacter saccharoketogenes* 12-4 strain: FERM BP-1131, IFO 14483

*Pseudogluconobacter saccharoketogenes* 22-3 strain: FERM BP-1133, IFO 11484.

As described above, in this method, microbial cells of a microorganism belonging to the genus Pseudogluconobacter per se can be used. Alternatively, their processed materials can also be used. Examples of the processed materials include a culture broth of the microorganism. In addition, enzymes produced by the microorganism can also be used. In the case of a microorganism of Pseudogluconobacter, normally, the enzyme is accumulated intracellularly. Conveniently, microbial cells per se are normally used and they are contacted and reacted with a saccharide starting material to form the corresponding carboxylic acid. In particular, it is preferred to use resting cells.

Such cells and culture broth thereof can be prepared in accordance with the method described in JP-A 1-85088. That is, a seed culture is prepared from a slant culture and main cultivation is carried out to obtain a culture broth. If necessary, the culture broth is centrifuged, followed by collecting the precipitate and rinsing the precipitate several times with a saline solution. The resulting precipitate can be used for the microbial reaction. The microorganism can be cultivated under aerobic conditions in a liquid medium containing assimilable nutrients, that is, carbon sources such as carbohydrates (e.g., glucose, sucrose, starch, etc.) or organic materials (e.g., peptone, yeast extract, etc.); nitrogen sources such as inorganic and organic nitrogen containing compounds (e.g., ammonium salts, urea, corn steep liquor, peptone, etc.); inorganic salts such as salts of potassium, sodium, calcium, magnesium, iron, manganese, cobalt, copper, phosphate, thiosulfate, etc., and, as trace nutrients, vitamins and coenzymes such as CoA, pantothenic acid, biotin, thiamin, riboflavin, FMN (flavin mononucleotide), etc., amino acids such as L-cysteine, L-glutamic acid, etc., or natural substances containing them. The culture broth per se thus obtained can be used. The cultivation is carried out at pH 4 to 9, preferably, pH 6 to 8.

Although the cultivation time varies depending upon a particular microorganism used, a particular composition of culture medium, etc., it is preferably 10 to 100 hours. The incubation temperature is suitably in the range of 10° to 40° C., preferably in the range of 25° to 35° C. Upon cultivation, when at least one rare earth element is added to a culture medium, the desired product can be produced more efficiently. Examples of rare earth elements to be added to the culture medium include scandium (Sc), yttrium (Y), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), lutetium (Uu), etc. These rare earth elements can be added in the form of powdered metals or metallic pieces, or they can be used as compounds containing them such as their chlorides, carbonates, sulfates, nitrates, oxides and oxalates. They can be used alone or in combination thereof, for example, cerium carbonate and lanthanum chloride can be used simultaneously. In addition, a crude material obtained during the separation and purification of these elements can also be used. The amount of the rare earth element or elements to be added to the culture medium can be selected from a range in which the growth of the microorganism to be used is not inhibited and, normally, the range of 0.000001 to 0.1% (w/v), preferably, 0.0001 to 0.05% (w/v) is effective. The element or elements can be added to the culture medium beforehand. Alternatively, they can be continuously or intermittently added to the culture medium during incubation.

The saccharide to be subjected to the reaction is dissolved or suspended in water or a water miscible solvent, for example, methanol, acetone, polyethylene glycol, etc., and the resulting solution or suspension can be contacted with the microorganism. The amount of the solvent to be used is not specifically limited insofar as the reaction is not delayed and, normally, the substrate concentration range of 0.1 to 20% (w/v), preferably, 1 to 5% (w/v) is effective. The microbial oxidation reaction is suitably carried out at 10° to 40° C., preferably, 25° to 35° C. Preferably, the reaction is carried out under aerobic conditions and, for example, is carried out by aeration at the rate of 0.1 to 5 liters/minute, if necessary, with stirring at 50 to 2,000 r.p.m. Although the reaction time varies depending upon the nature of the primary hydroxy group and/or hemiacetal hydroxyl group of the saccharide used, the reaction is carried out for 5 minutes to 3 days, normally, 1 to 24 hours. The reaction pH is preferably adjusted. Normally, the reaction is carried out at pH 4 to 9, preferably, at pH 6 to 8. Any base can be used for adjusting the reaction pH insofar as the reaction is not inhibited. Examples of the base include inorganic bases such as sodium hydroxide, potassium hydroxide, calcium carbonate, magnesium hydroxide, ferrous hydroxide, etc., organic bases such as sodium morpholinoethane sulfonate, calcium morpholinoethane sulfonate, etc.

Optionally, an anion exchange resin can also be added to selectively control the reaction without using a neutralizing agent such as the above alkaline metal salt for adjusting pH. In particular, when the selective reaction is carried out to obtain one equivalent of the oxidized product, this addition of an anion exchange resin is preferred. Any anion exchange resin can be used insofar as it can adsorb the carboxylic acid produced. In particular, styrene type and acrylic anion exchange resins are preferred. Examples thereof include Amberlite (trade name, Organo Corp.) IRA-400, IRA-401, IRA-402, IRA-410, IRA-900, IRA-910, IRA-35, IRA-68, IRA-94S, etc., and Diaion (trade name, Mitsubisi Kasei Corp.) SA-10A, SA-20A, PA-306, PA-308, PA-406, WA-10, WA-11, WA-20, WA-30, etc.

When the saccharide added as the substrate (i.e., a monosaccharide derivative having a hydroxymethyl group and/or hemiacetal hydroxyl moiety, an oligosaccharide or its derivative, or a polysaccharide or its derivative) has disappeared in a reaction mixture, stirring is stopped, and the anion exchange resin is separated from the reaction mixture and eluted with a suitable solvent to obtain the desired product. Examples of the eluent include an aqueous solution such as saline solution or an aqueous solution of an alkali metal salt; or an acidic aqueous solution of hydrochloric acid, sulfuric acid, phosphoric acid, citric acid, etc. The saccharide-carboxylic acid thus eluted and accumulated can be collected and purified according to a known method or its modification.

When the above saccharide as the starting material is contacted with the above microorganism belonging to the genus Pseudogluconobacter or its processed material to carry out the oxidation, the sacchaide is oxidized regiospecifically and stepwise to give the corresponding saccharide-carboxylic acid depending on the number or nature of the primary hydroxyl group or hemiacetal hydroxyl moiety. This is characteristic of the oxidation by the microbial cells belonging to the genus Pseudogluconobacter or a processed material thereof.

When the desired product can easily be separated, the above microorganism belonging to the genus Pseudogluconobacter can be cultivated in the culture medium containing the above saccharide. The cultivation can be carried out under similar conditions to those used in the preparation of the above culture.

The cyclodextrin-carboxylic acid thus produced and accumulated can be collected and purified by a known method or its modification. For example, the desired product can be isolated and purified by conventional means such as filtration, centrifugation, treatments with activated charcoal or adsorbents, solvent extraction, chromatography, precipitation, salting out, etc., alone or in combination thereof.

As described above, when the oxidation is carried out in the presence of an anion exchange resin, the reaction mixture is allowed to stand or centrifuged to separate the anion exchange resin from the reaction mixture. Then, the anion exchange resin is eluted with an eluent, the eluted fractions containing the desired product are combined, and the desired cyclodextrin-carboxylic acid is isolated and purified by the above known means or their modification.

The desired cyclodextrin-carboxylic acid may be obtained as its free carboxylic acid or its salt. When it is obtained as its free carboxylic acid, the free carboxylic acid can be converted to its salt by conventional methods. When it is obtained as its salt, the salt can be converted to the corresponding free carboxylic acid. Alternatively, when the cultivation is carried out in the presence of an alkali metal such as iron, lithium, sodium or potassium, or an alkaline earth metal such as magnesium or calcium, a salt of the saccharide-carboxylic acid can form while producing and accumulating the saccharide-carboxylic acid. The product thus obtained can be identified based on conventional means such as elemental analysis, melting point, specific rotatory power, infrared absorption spectrum, NMR spectrum, chromatography, etc.

Other saccharides such as $\alpha$-CyD-$G_1$-COOH, $\beta$-CyD-$G_1$-COOH, $\gamma$-CyD-$G_1$-COOH, $\alpha$-CyD-$CH_2$COOH, $\beta$-CyD-$CH_2$COOH, $\gamma$-CyD-$CH_2$COOH, 3-hydroxypropyl-$\beta$-CyD-COOH, 2,3-dihydroxypropyl-$\beta$-CyD-COOH and dimaltosyl-$\beta$-CyD-COOH or salts thereof can be produced according to substantially the same manner as that described above.

It is known that water solubility can be increased by introducing a substituent such as maltose, glucose, 3-hydroxypropyl, 2,3-dihydroxypropyl, etc., as a branched chain into a cyclodextrin ring. For example, the water-solubility of $G_2$-$\beta$-CyD is several tens of times that of $\beta$-cyclodextrin. However, it has been found that the water-solubility can further be increased by oxidizing the hydroxy-lmethyl group at the 6-position of the terminal maltose of $G_2$-$\beta$-CyD to obtain the corresponding cyclodextrin-carboxylic acid or its salt. For example, the saccharide-carboxylic acid derivative of maltosyl-$\beta$-cyclodextrin, which is the first carboxylic acid derivative of cyclodextrins, has a significantly increased water-solubility (>200 g/100 ml water, 25° C.). In other words, it has been found that solubility in water can be greatly increased by using the branched cyclodextrin-carboxylic acids of the present invention, and that, as a result, an inclusion compound containing $\beta$-CyD-$G_2$-COOH and/or a salt thereof as a host compound has a much higher water-solubility than that of an inclusion compound containing $\beta$-cyclodextrin as a host compound, Thus, it is possible to obtain an aqueous solution of a water-insoluble or slightly water-soluble compound in a very high concentration.

Moreover, it has also been found that these novel cyclodextrin-carboxylic acids have lower toxicity than that of known cyclodextrins, have a less harmful effect (e.g., destruction of erythrocytes) on the living body than that of $\beta$-cyclodextrin, have high safety to blood, and are hardly decomposed by acids or enzymes.

Thus, in the present invention, the water-solubility of a water-insoluble or slightly water-soluble compound can be enhanced by formulating it together with a branched cyclodextrin-carboxylic acid in a composition.

The water-insoluble or slightly water-soluble compound to be used is not specifically limited and is appropriately selected from drugs useful as active ingredients of medicaments that are insoluble or slightly soluble in water as well as compounds useful as active ingredients of cosmetics, food and drink, agricultural chemicals, veterinary drugs, etc., that need enhancement of their water-solubility.

As the water-insoluble or slightly water-soluble compounds, there are usually used compounds having a water-solubility of not more than 10 mg/ml, which need enhancement of the solubility.

Examples of the water-insoluble or slightly water-soluble drugs useful as active ingredients of medicaments or veterinary drugs include antipyretic analgesic anti-inflammatory agents such as salicylic acid, sulpyrine, flufenamic acid, diclofenac, indomethacin, chlorpromazine, prochloroperazine, trifluoperazine, atropine, scopolamine, morphine, pethidine, levorphanol, oxymorphone, or its salts thereof, etc.; tranquilizers such as diazepam, lorazepam, oxazepam, etc.; antimicrobial agents such as griseofulvin, lankacidins (J. Antibiotics, 38, 877–885 (1985)), azole compounds (e.g., 2-[1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3-(2H,4H)-1,2,4-triazolone, fluconazole, itraconazole, etc.), etc.; antibiotics such as gentamicin, dibekacin, kanendomycin, lividomycin, tobramycin, amikacin, fradiomycin, sisomicin, tetracycline, oxytetracycline, rolitetracycline, doxycycline, ampicillin, piperacillin, ticarcillin, cefalothin, cephaloridine, cefotiam hexetyl, cefsulodin, cefmenoxime, cefmetazole, cefazolin, cefotaxime, cefoperazone, ceftizoxime, moxalactam, thienamycin, sulfazecin, azthreonam, or salts thereof, etc.; antineoplastic agents such as 6-O-(N-chloroacetylcarbamoyl)-fumagillol, bleomycin, methotrexate, actinomycin D, mitomycin C, daunorubicin, adriamycin, neocarzinostatin, cytosine arabinoside, fluorouracil, tetrahydrofuryl-5-fluorouracil, picibanil, lentinan, levamisole, bestatin, azimexon, glycyrrhizin, etc.; antilipemic agents such as clofibrate, ethyl 2-chloro-3-[4-(2-methyl-2-phenylpropyloxy)phenyl]-propionate (Chem.

Pharm. Bull., 38, 2792–2796 (1990)), etc.; antitussive expectorants such as ephedrine, methylephedrine, noscapine, codeine, dihydrocodeine, alloclamide, chlorphezianol, picoperidamine, cloperastine, protokylol, isoproterenol, salbutamol, terbutaline, or salts thereof, etc.; muscle relaxants such as pridinol, tubocurarine, pancuronium, etc.; antiepileptic agents such as phenytoin, ethosuximide, acetazolamide, chlordiazepoxide, etc.; antiulcerative agents such as metoclopramide, etc.; antidepressants such as imipramine, chlomipramine, noxiptiline, phenelzine, etc.; antiallergic agents such as diphenhydramine, chlorpheniramine, tripelennamine, methdilamine, clemizole, diphenylpyraline, methoxyphenamine, etc.; cardiacs such as transbioxocamphor, theophyllol, aminophylline, etilefrine, etc.; antiarrhythmic agents such as propranolol, alprenolol, bufetolol, oxprenolol, etc.; vasodilators such as oxyphedrin, diltiazem, tolazoline, hexobendine, bamethan, etc.; hypotensive diuretics such as hexamethonium bromide, pentolinium, mecamylamine, ecarazine, clonidine, etc.; antidiabetic agents such as glymidine, glipzide, phenfdrmin, buformin, metformin, etc.; antitubercular agents such as isoniazid, ethambutol, p-aminosalicylic acid, etc.; narcotic antagonists such as levallorphan, nalorphine, naloxone, or salts thereof, etc.; hormone preparations such as steroid hormones (e.g., dexamethasone, hexestrol, methimazole, betamethasone, triamcinolone, triamcinolone acetonide, fluocinolone acetonide, prednisolone, hydrocortisone, estriol, etc.); fat soluble vitamins such as vitamin As (e.g., vitamin $A_1$, vitamin $A_2$, retinol palmitate, etc.), vitamin Ds (e.g., vitamins $D_1$, $D_2$, $D_3$, $D_4$ and $D_5$, etc.), vitamin Es (e.g., α-tocopherol, β-tocopherol, γ-tocopherol, δ-tocopherol and dl-α-tocopherol nicotinate), vitamin Ks (e.g., vitamins $K_1$, $K_2$, $K_3$ and $K_4$), folic acid (vitamin M), etc. Various derivatives of the above vitamins can also be used. Examples of the vitamin derivatives include vitamin $D_3$ derivatives such as 5,6-trans-cholecalciferol, 25-hydroxycholecalciferol, 1-α-hydroxycholecalciferol, etc.; vitamin $D_2$ derivatives such as 5,6-trans-ergocalciferol, etc.

Other examples of the slightly water-soluble drugs include piroxicam, diacerein, diltiazem, megestrol acetate, nifedipine, nicergoline, ketoprofen, naproxen, ibuprofen, prostaglandins, etc.

Examples of the water-insoluble or slightly water-soluble compounds useful as active ingredients of cosmetics include methyl cinnamate, ethyl cinnamate, dl-α-tocopherol acetate, α-tocopherol (vitamin E), trichlorocarbanilide, eugenol, isoeugenol, ethyl methylphenylglycidate, geranyl acetate, piperonal, hexyl laurate, ionone, cinnamyl acetate, decyl oleate, terpinyl acetate, etc.

Examples of the water-insoluble or slightly water-soluble compounds useful as active ingredients of agricultural chemicals include benomyl, carbendazim, fuberidazole, thiophanate, thiophanate methyl, triarimol, prochloraz, oxadixyl, dazomet, captan, captafol, quinomethionate, Vancor (registered trade mark), probenazole, diethofencarb, ferimzone, etc.

Examples of the water-insoluble or slightly water-soluble compounds useful as active ingredients of food or drink include L-ascorbyl stearate, benzoic acid, ionone, isoeugenol, ergocalciferol (vitamin $D_2$), eugenol, butyl p-hydroxybenzoate, isopropyl p-hydroxybenzoate, β-carotene, citronellyl formate, cholecalciferol (vitamin $D_3$), cinnamyl acetate, phenethyl acetate, ethyl cinnamate, dibutyl hydroxy toluene, vitamin A oil, allyl hexanoate, propyl gallate, methyl β-methyl ketone, folic acid, riboflavine tetrabutyrate, lecithin, dl-α-tocophelol, etc.

In the present invention, the mixing ratio of the branched cyclodextrin-carboxylic acid to the water-insoluble or slightly water-soluble compound is not limited and can be selected from wide ranges. However, considering the water-solubility of the water-insoluble or slightly water-soluble compounds, the amount of the branched cyclodextrin-carboxylic acid to be used is 0.1 to 20 mol, preferably 0.1 to 10 mol, more preferably 0.2 to 5 mol, particularly preferably 1 to 2 mol, per mol of the water-insoluble or slightly water-soluble compound.

The composition of the present invention can be prepared by mixing the branched cyclodextrin-carboxylic acid with the water-insoluble or slightly water-soluble compound according to known methods. Roughly speaking, the inclusion compound of the water-insoluble or slightly water-soluble compound included in the branched cyclodextrin-carboxylic acid can be prepared, for example, by the following four methods:

(1) Co-precipitation method (Crassons, et al., 5th Int. Conf. Pharmaceutical Technology, Paris, May 30 to Jun. 1, 1989), (2) Lyophilizing or spray drying method (Kurozumi et al., Chem. Pharm. Bull., 23, 3062 (1975); Kata et al., Pharmazie 39, 856 (1984)), (3) Phase-solubility curve crystallization method (Uekama et al., Int. J. Pharmc. 10,1 (1982)), (4) Milling method (J. Szejtli et al., "Cyclodextrins and their inclusion complexes", Akadeimial Kiado, Budapest (1982), p. 109–114; Kyowa Jap. Prov. Pat. Pubin. No. 106 698 (1982)).

Specifically, the inclusion compound can be prepared as follows:

(1) A compound to be included in the inclusion compound is added to an aqueous solution of the branched cyclodextrin-carboxylic acid (hereinafter sometimes referred to as the cyclodextrin). The mixture is stirred (shaken), if necessary, under warming. The remaining unreacted compound to be included is removed by filtration, centrifugation, etc., to obtain an inclusion compound.

(2) The cyclodextrin is dissolved in water, and a compound to be included is added thereto. The two are mixed for 10 minutes to several hours, followed by lyophilization (M. Kurozumi et al., Chem. Pharm. Bull., 23, 142 (1975)) to give powder. This powder is dissolved in water, and the unreacted compound to be included is removed to obtain an aqueous solution of an inclusion compound.

(3) A compound to be included is dissolved in an appropriate water-soluble organic solvent in advance. This solution is contacted with cyclodextrin in an aqueous solution. Then the organic solvent and water are evaporated in vacuo or lyophilized (EP-A-519428, JP-A 5 (1992)-178765 (Japanese Patent Application No. 03-150507), Japanese Patent Application No. 03-230489)), and water is then added to the residue to dissolve it, and the unreacted compound to be included is removed to obtain an aqueous solution of an inclusion compound.

(4) When an acidic compound is included in the inclusion compound, it is dissolved in ammonia water and cyclodextrin is added thereto, and the mixture is lyophilized. During the lyophilization, excess ammonia is removed and an inclusion compound is obtained as an ammonium salt of the acidic compound.

(5) A compound to be included is dissolved in a lipophilic organic solvent (e.g., ethyl ether, etc.), and the solution is mixed with a saturated aqueous solution of the cyclodextrin.

The mixture is shaken vigorously for 10 minutes to several hours and then allowed to stand in a cold place overnight to precipitate an inclusion compound. The precipitate is separated by centrifugation or filtration. The resulting powder is dissolved in water to give an aqueous solution of an inclusion compound.

(6) A powdered compound to be included and powdered cyclodextrin are mixed, and a small amount of water is added thereto. The mixture is kneaded (Y. Nakai et al., Chem. Pharm. Bull., 26, 2419 (1978)) and then, if necessary, lyophilized.

(7) An aqueous solution of the cyclodextrin and an aqueous solution of a compound to be included are mixed to give an aqueous solution of an inclusion compound.

In many cases, the aqueous solution or powder thus obtained by the known methods giving inclusion compounds contains an inclusion compound or a complex formed by electrostatic or hydrophobic interactions or hydrogen bonds, etc. Therefore, the term "inclusion compound" used in the present invention means not only an inclusion compound or a complex per se but also a mixture of an inclusion compound, a complex, a free compound to be included and/or a free cyclodextrin. That is, the powder and aqueous solution obtained may contain, other than an inclusion compound or a complex, a water-insoluble or slightly water-soluble compound that is not included or complexed, and/or free cyclodextrin. The inclusion compound per se and powder and an aqueous solution like this have extremely high water-solubilities and dissolve in water instantly.

The composition of the present invention may be the aqueous solution or powder per se thus obtained, or, if necessary, it may be a pharmaceutical composition in an appropriate dosage form, a cosmetic composition, a composition for eating or drinking, an agricultural composition, a veterinary composition, etc., prepared using known additives such as excipients, binders or lubricants.

For example, to improve properties of the powder obtained above (packing capacity into a storage bottle or a vial, specific volume, destaticizing, etc.), saccharides, antiseptics, stabilizers, antistatic agents, etc., can be added. For example, when injections are prepared, the powder obtained by this operation readily dissolves in an aqueous isotonic solution prepared using distilled water or sodium chloride and saccharides (e.g., glucose, mannitol, inositol, etc.). After dissolution, the resulting injectable preparation containing an active ingredient can be administered intravenously, intramuscularly, subcutaneously, into organs, or directly to foci such as tumor or excised parts of tumor, in a drug concentration effective in vivo against the diseases to be treated. When oral preparations are prepared, tablets, capsules, granules, fine granules, enveloped preparations, drops, liquids, etc., can be prepared. On formulating these preparations, known excipients, lubricants, binders, dispersers, stabilizers, colorants and absorption-improving (promoting) agents, etc., can normally be used.

The above powder can also be formulated into preparations other than injectable or oral preparations according to conventional methods. Examples of such preparations are preparations administered to mucous membranes such as nose, the oral cavity, sublingual parts, the rectum, the vagina or the uterus, percutaneous preparations, and implants. Each of the above preparations can be molded into various controlled-release preparations or preparations for targeting therapies, and the composition of the present invention can be used as a raw material of such preparations.

As described above, the branched cyclodextrin-carboxylic acid used in the present invention enhances the water-solubility of a water-insoluble or slightly water-soluble compound and has high safety to the living body. Therefore, it is extremely useful for pharmaceutical compositions or veterinary compositions in various dosage forms such as injections, oral preparations, preparations administered to the oral cavity (e.g., troches, buccals, etc.), sublingual preparations, eye drops, syrups, preparations externally administered to skin, pernasal preparations, preparations administered via the lungs, rectal suppositories or preparations applied to mucous membranes, and are useful as drugs for use in humans or mammals other than humans (e.g., monkeys, cattle, dogs, etc.).

Like pharmaceutical compositions or veterinary compositions, cosmetic compositions, agricultural compositions, compositions for eating or drinking, etc., can be prepared by conventional methods using appropriate additives.

As described above, a water-insoluble or slightly water-soluble compound combined with a branched cyclodextrin-carboxylic acid according to the present invention has a much higher water-solubility compared with that of the water-insoluble or slightly water-soluble compound alone. Further, for example, $\beta$-CyD-G$_2$-COOH improves the water-solubility of a water-insoluble or slightly water-soluble compound by several tens of times that of the water-insoluble or slightly water-soluble compound combined with $\beta$-cyclodextrin. In addition, the branched cyclodextrin-carboxylic acid has less effect (e.g., destruction of erythrocytes) on the living body than $\beta$-cyclodextrin, and therefore is highly safe for blood. Moreover, $\beta$-CyD-G$_2$-COOH is hardly decomposed with acids or enzymes, and therefore the composition of the present invention is highly safe to mammals including humans.

The following examples, experiments and reference examples further illustrate the present invention in detail, but are not to be construed to limit the scope thereof.

EXAMPLE 1

The antineoplastic agent 6-O-(N-chloroacetyl-carbamoyl) fumagillol (100 mg) was dissolved in ethanol (4 ml). Separately from this solution, each of sodium 6-O-cyclomaltoheptaosyl-(6→1)-$\alpha$-D-glucosyl-(4→1)-O-$\alpha$-D-glucuronate ($\beta$-CyD-G$_2$-COONa) (744 mg) and $\beta$-cyclodextrin (hereinafter abbreviated as $\beta$-CyD) (579 mg) was separately dissolved in water (15 ml) (the antineoplastic agent: $\beta$-CyD-G$_2$-COONa or $\beta$-CyD=1:2 (mol ratio)). The aqueous solution was added to the ethanol solution and mixed with it with stirring. The resulting solution was lyophilized in vacuo to give powder. Water (1 ml) was added to the powder (100 mg) to obtain a homogeneous aqueous solution, i.e., a composition of the present invention.

On the other hand, the antineoplastic agent alone was added to water, and the mixture was vigorously shaken at 25° C. for 4 hours and filtered through a membrane filter of 0.22 $\mu$m.

The antineoplastic agent in the above homogeneous aqueous solution and filtrate was determined by high performance liquid chromatography (HPLC). As a result, the solubilities in Table 1 were obtained.

TABLE 1

Comparison of the solubilities of the antineoplastic agent

| | |
|---|---|
| Present invention | 39.7 mg/ml |
| Antineoplastic agent combined with β-CyD | 16.3 |
| Antineoplastic agent alone | 1.8 |

As shown in Table 1, addition of β-CyD-G$_2$-COONa remarkably increased the water-solubility of the antineoplastic agent compared with the case in which the antineoplastic agent was used alone or in combination with β-CyD.

EXAMPLE 2

According to the same manner as that described in Example 1, the antineoplastic agent 6-O-(N-chloroacetylcarbamoyl)fumagillol (100 mg) was dissolved in ethanol (4 ml). Separately from this solutions each of sodium 6-O-cyclomaltohexaosyl-(6→1)-α-D-glucosyl-(4→1)-O-α-D-glucuronate (hereinafter abbreviated as α-CyD-G$_2$-COONa) (622 mg), and α-cyclodextrin (hereinafter abbreviated as α-CyD) (642 mg) was separately dissolved in water (15 ml) (the antineoplastic agent: α-CyD-G$_2$-COONa or α-CyD=1:2 (mol ratio)). The aqueous solution was added to the ethanol solution and mixed with it with stirring. The resulting solution was lyophilized in vacuo to give powder. Water (1 ml) was added to the powder (100 mg) to obtain a homogeneous aqueous solution, i.e., a composition of the present invention. On the other hand, the antineoplastic agent alone was added to water, and the mixture was vigorously shaken at 25° C. for 4 hours and filtered through a membrane filter of 0.22 μm.

The antineoplastic agent in the above homogeneous aqueous solution and filtrate was determined by high performance liquid chromatography (HPLC). As a result, the solubilities in Table 2 were obtained.

TABLE 2

Comparison of the solubilities of the antineoplastic agent

| | |
|---|---|
| Present invention | 32.1 mg/ml |
| Antineoplastic agent combined with α-CyD | 13.6 |
| Antineoplastic agent alone | 1.8 |

As shown in Table 2, addition of α-CyD-G$_2$-COONa remarkably increased the water-solubility of the antineoplastic agent compared with the case in which the antineoplastic agent was used alone or in combination with α-CyD.

EXAMPLE 3

According to the same manner as that described in Example 1, the cephalosporin antibiotic (-)-7β-[(Z)-2-(5-amino-1,2,4-thiadiazol-3-yl)-2-methoxyiminoacetamide]-3-(1-imidazo[1,2-b]pyridazinium)methyl-3-cephem-4-carboxylate (100 mg; free form) was dissolved in ethanol (4 ml). Separately, each of sodium 6-O-cyclomaltoheptaosyl-(61)-α-D-glucosyl-(4→1)-O-α-D-glucuronate (β-CyD-G$_2$-COONa) (580 mg) and β-cyclodextrin (β-CyD) (451 mg) was dissolved in water (15 ml) (the antineoplastic agent: β-CyD-G$_2$-COONa or β-CyD=1:2 molar ratio). The aqueous solution was added to the ethanol solution and mixed with it with stirring. The resulting solution was lyophilized in vacuo to give powder. Water (1 ml) was added to the powder (100 mg) to obtain a homogeneous aqueous solution, i.e., a composition of the present invention. On the other hand, the antibiotic alone was added to water, and the mixture was vigorously shaken at 25° C. for 8 hours and filtered through a membrane filter of 0.22 μm.

The antibiotic in the above homogeneous aqueous solution and filtrate was determined by high performance liquid chromatography (HPLC). As a result, the solubilities in Table 3 were obtained.

TABLE 3

Comparison of the solubilities of the antibiotic

| | |
|---|---|
| Present invention | 38 mg/ml |
| Antineoplastic agent combined with β-CyD | 14 |
| Antineoplastic agent alone | 2.5 |

As shown in Table 3, addition of β-CyD-G$_2$-COONa remarkably increased the water-solubility of the antibiotic compared with the case in which the antibiotic was used alone or in combination with β-CyD.

EXAMPLE 4

According to the same manner as that described in Example 1, lyophilized powder was obtained from the antifungal agent 2-[(1R,2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl]-3-(2H,4H)-1,2,4-triazolone (100 mg) andsodium 6-O-cyclomaltoheptaosyl-(6→1)-α-D-glucosyl-(4→1)-O-α-D-glucuronate (β-CyD-G$_2$-COONa) (551 mg) (the antifungal agent: β-CyD-G$_2$-COONa=1:2 (molar ratio)). Likewise, lyophilized powder was obtained from the antifungal agent and β-cyclodextrin (β-CyD) (the antifungal agent: β-CyD=1:2 (molar ratio)). According to the same manner as that described in Example 1, the water-solubilities of these powder and the antifungal agent alone were measured. The results are in Table 4.

TABLE 4

Comparison of the solubilities of the antifungal agent

| | |
|---|---|
| Present invention | 0.32 mg/ml |
| Antifungal agent combined with β-CyD | 0.12 |
| Antifungal agent alone | 0.005 |

As shown in Table 4, addition of β-CyD-G$_2$-COONa remarkably increased the water-solubility of the antifungal agent compared with the case in which the antifungal agent was used alone or in combination with β-CyD.

EXAMPLE 5

According to the same manner as that described in Example 1, lyophilized powder was obtained from the antilipemic agent clofibrate (100 mg) and sodium 6-O-cyclomaltoheptaosyl-(6→1)-α-D-glucosyl-(4→1)-O-α-D-glucuronate (β-CyD-G$_2$-COONa) (1232 mg) (clofibrate: β-CyD-G$_2$-COONa=1:2 (molar ratio)). Likewise, lyophilized powder was obtained from clofibrate and β-cyclodextrin (β-CyD) (clofibrate: β-CyD=1:2 (molar ratio)). According to the same manner as that described in Example 1, the water-solubilities of these powder and clofibrate alone were measured. The results are in Table 5.

TABLE 5

Comparison of the solubilities of clofibrate

| | |
|---|---|
| Present invention | 4.18 mg/ml |
| Clofibrate combined with β-CyD | 0.161 |
| Clofibrate agent alone | 0.082 |

As shown in Table 5, addition of β-CyD-G$_2$-COONa remarkably increased the water-solubility of clofibrate compared with the case in which clofibrate was used alone or in combination with β-CyD.

EXAMPLE 6

Sodium 6-O-cyclomaltoheptaosyl-(6→1)-O-α-D-glucosyl-(4→1)-O-α-D-glucuronate (β-CyD-G$_2$-COONa) (75 mg) was dissolved in water (5 ml). The tranquilizer diazepam (about 3 mg) was added, and the mixture was shaken vigorously at 25° C. for 8 hours, centrifuged and filtered through Millipore filter (0.22 μm) to separate the supernatant. Using β-cyclodextrin (β-CyD) in place of the above β-CyD-G$_2$-COONa and using diazepam alone, the same procedure was carried out, and the concentration of diazepam dissolved in the resulting filtrate was determined by HPLC. The results are in Table 6.

TABLE 6

Comparison of the solubilities of diazepam

| | |
|---|---|
| Present invention | 0.511 mg/ml |
| Diazepam combined with β-CyD | 0.198 |
| Diazepam alone | 0.055 |

As shown in Table 6, addition of β-CyD-G$_2$-COONa remarkably increased the water-solubility of diazepam compared with the case in which diazepam was used alone or in combination with β-CyD.

EXAMPLE 7

According to the same manner as that described in Example 6 except using the antiinflammatory agent flufenamic acid (about 6 mg) instead of diazepam, the water-solubility of flufenamic acid alone or in combination with β-CyD-G$_2$-COONa or β-cyclodextrin was determined. The results are in Table 7.

TABLE 7

Comparison of the solubilities of flufenamic acid

| | |
|---|---|
| Present invention | 2.11 mg/ml |
| Flufenamic acid combined with β-CyD | 0.81 |
| Flufenamic acid alone | 0.074 |

As shown in Table 7, addition of β-CyD-G$_2$-COONa remarkably increased the water-solubility of flufenamic acid compared with the case in which flufenamic acid was used alone or in combination with β-CyD.

EXAMPLE 8

According to the same manner as that described in Example 6 except using the hormone preparation testosterone (about 6 mg) instead of diazepam, the water-solubility of testosterone alone or in combination with β-CyD-G$_2$-COONa or β-CyD was determined. The results are in Table 8.

TABLE 8

Comparison of the solubilities of testosterone

| | |
|---|---|
| Present invention | 1.42 mg/ml |
| Testosterone combined with β-CyD | 0.086 |
| Testosterone alone | 0.029 |

As shown in Table 8, addition of β-CyD-G$_2$-COONa remarkably increased the water-solubility of testosterone compared with the case in which testosterone was used alone or in combination with β-CyD.

EXAMPLE 9

According to the same manner as that described in Example 6 except using the antiepileptic agent phenytoin (about 4 mg) instead of diazepam, the water-solubility of phenytoin alone or in combination with β-CyD-G$_2$-COONa or β-CyD was determined. The results are in Table 9.

TABLE 9

Comparison of the solubilities of phenytoin

| | |
|---|---|
| Present invention | 896 μg/ml |
| Phenytoin combined with β-CyD | 281 |
| Phenytoin alone | 27 |

As shown in Table 9, addition of β-CyD-G$_2$-COONa remarkably increased the water-solubility of phenytoin compared with the case in which phenytoin was used alone or in combination with β-CyD.

EXAMPLE 10

According to the same manner as that described in Example 6 except using vitamin K$_2$ (about 2 mg), a fat-soluble vitamin, instead of diazepam, the water-solubility of vitamin K$_2$ alone or in combination with β-CyD-G$_2$-COONa or β-CyD was determined. The results are in Table 10.

TABLE 10

Comparison of the solubilities of vitamin K$_2$

| | |
|---|---|
| Present invention | 67.4 μg/ml |
| Vitamin K$_2$ combined with β-CyD | 0.001 |
| Vitamin K$_2$ alone | 0.0005 |

As shown in Table 10, addition of β-CyD-G$_2$-COONa remarkably increased the water-solubility of vitamin K$_2$ compared with the case in which vitamin K$_2$ was used alone or in combination with β-CyD.

EXAMPLE 11

According to the same manner as that described in Example 6 except using the antiinflammatory agent indomethacin (about 4 mg) instead of diazepam, the water-solubility of indomethacin alone or in combination with β-CyD-G$_2$-COONa or β-CyD was determined. The results are in Table 11.

TABLE 11

Comparison of the solubilities of indomethacin

| | |
|---|---|
| Present invention | 134 μg/ml |
| Indomethacin combined with β-CyD | 54 |
| Indomethacin alone | 23 |

As shown in Table 11, addition of β-CyD-G$_2$-COONa remarkably increased the water-solubility of indomethacin compared with the case in which indomethacin was used alone or in combination with β-CyD.

EXAMPLE 12

To the antifungal agent griseofulvin (100 mg) was added sodium 6-O-cyclomaltoheptaosyl-(6→1)-α-D-glucosyl-(4→1)-O-α-D-glucuronic acid (β-CyD-G$_2$-COONa) (313 mg) (griseofulvin: β-CyD-G$_2$-COONa=1:1 (molar ratio)). The two components were mixed, and the mixture was added to a tumbler pulverizer (stainless steel cylinder (30 mm φ×50 mm), five stainless balls (each 10 mm φ)). A small amount of water (distilled water) was added thereto, and the resulting mixture was vigorously shaken at a shaking rate of 300 shakes/minute for about 6 hours and lyophilized in vacuo to give powder. Separately, powder was obtained in the same manner except using β-cyclodextrin (hereinafter abbreviated as β-CyD) (238 mg) (griseofulvin: β-CyD=1:1 (molar ratio)) instead of β-CyD-G$_2$-COONa. Water (1 ml) was added to each powder (100 mg) thus obtained to obtain an aqueous solution thereof. On the other hand, griseofulvin alone was added to water, and the mixture was vigorously shaken at 25° C. for 6 hours and filtered through a membrane filter of 0.22 μm.

The griseofulvin in the above filtrate was determined by spectrophotometry (Shimadzu Corp., Uv-240 spectrophotometer). The results are in Table 12.

TABLE 12

Comparison of the solubilities of griseofulvin

| | |
|---|---|
| Present invention | 410 μg/ml |
| Griseofulvin combined with β-CyD | 30 |
| Griseofulvin alone | 23 |

As shown in Table 12, addition of β-CyD-G$_2$-COONa remarkably increased the water-solubility of griseofulvin compared with the case in which griseofulvin was used alone or in combination with β-CyD.

EXAMPLE 13

According to the same operation and using the same apparatus as those in Example 12, β-CyD-G$_2$-COONa (230 mg) was added to the antidiabetic agent acetohexamide (50 mg) (acetohexamide:G$_2$-β-CyD-COONa=1:1 (molar ratio)), and the mixture was shaken and lyophilized in vacuo to give powder. Separately, powder was obtained by the same operation except using β-CyD instead of the above β-CyD-G$_2$-COONa. Water (1 ml) was added to each powder (100 mg) thus obtained to dissolve it. On the other hand, acetohexamide alone was added to water, and the mixture was vigorously shaken at 25° C. for 6 hours and filtered through a membrane filter of 0.22 μm. The acetohexamide in the above filtrate was determined with an ultraviolet spectrophotometer (Shimadzu Corp., UV-240). The results are in Table 13.

TABLE 13

Comparison of the solubilities of acetohexamide

| | |
|---|---|
| Present invention | 211.6 μg/ml |
| Acetohexamide combined with β-CyD | 81.4 |
| Acetohexamide alone | 28.1 |

As shown in Table 13, addition of β-CyD-G$_2$-COONa remarkably increased the water-solubility of acetohexamide compared with the case in which acetohexamide was used alone or in combination with β-CyD.

EXAMPLE 14

According to the same manner as that described in Example 6, sodium 6-O-cyclomaltohexaosyl-(6→1)-α-D-glucosyl-(4→1)-O-α-D-glucuronate (hereinafter abbreviated as α-CyD-G$_2$-COONa) (75 mg) was dissolved in water (5 ml), the hormone preparation testosterone (about 4 mg) was added thereto, and the mixture was vigorously shaken at 25° C. for 8 hours, centrifuged and filtered through Millipore filter (0.22 μm) to separate the supernatant. The same operations were carried out using α-cyclodextrin (α-CyD) instead of α-CyD-G$_2$-COONa or using testosterone alone. The concentration of testosterone dissolved in the resulting filtrate was determined with an ultraviolet spectrophotometer (Shimadzu Corp., UV-240). The results are in Table 14.

TABLE 14

Comparison of the solubilities of testosterone

| | |
|---|---|
| Present invention | 1.38 mg/ml |
| Testosterone combined with α-CyD | 0.22 |
| Testosterone alone | 0.029 |

As shown in Table 14, addition of α-CyD-G$_2$-COONa remarkably increased the water-solubility of testosterone compared with the case in which testosterone was used alone or in combination with α-CyD.

EXAMPLE 15

According to the same manner as that described in Example 6, sodium 2-hydroxy-3-O-(6-cyclomaltoheptaosyl)-propionate (hereinafter abbreviated as β-CyD-CH$_2$CH(OH)-COONa) (75 mg) was dissolved in water (5 ml), the hormone testosterone (about 4 mg) was added thereto, and the mixture was vigorously shaken at 25° C. for 8 hours, centrifuged and filtered through Millipore filter (0.22 μm) to separate the supernatant. The same operations were carried out using β-CyD instead of β-CyD-CH$_2$CH(OH)-COONa or using testosterone alone. The concentration of testosterone dissolved in the resulting filtrate was determined with an ultraviolet spectrophotometer (Shimadzu Corp., UV-240). The results are in Table 15.

TABLE 15

Comparison of the solubilities of testosterone

| | |
|---|---|
| Present invention | 940 μg/ml |
| Testosterone combined with β-CyD | 86 |
| Testosterone alone | 29 |

As shown in Table 15, addition of β-CyD-CH$_2$CH(OH)-COONa remarkably increased the water-solubility of testosterone compared with the case in which testosterone alone or β-CyD was added.

EXAMPLE 16

Powder lyophilized in vacuo was obtained from clofibrate (1 g) and β-CyD-G$_2$-COONa (12.3 g) according to the same manner as that described in Example 1. According to a conventional method for producing tablets, this powder was added to a container for kneading, and mixed with HPC-L (hydroxypropyl cellulose-L) (2 g), methylcellulose (6.5 g) and magnesium stearate (0.1 g). Purified water (5 ml) was further added, and the mixture was subjected to wet kneading and then dried in vacuo to give powder. Then, this powder was pulverized to give particles. 220 mg of the particles was placed in a tableting mortar (6 mm φ) and tableted at a tableting pressure of 1 ton to give 100 tablets of clofibrate (clofibrate 10 mg/tablet), i.e., the composition of the present invention.

EXAMPLE 17

Powder lyophilized in vacuo was obtained from diphenhydramine (5 g) and β-CyD-G$_2$-COONa (20 g) according to the same manner as that described in Example 1. According to a conventional method for producing nasal drops, this powder was dissolved in isotonic phosphate buffer (1000 ml, pH 7.4) prepared separately. Butyl p-hydroxybenzoate (0.005 g) was added as an antiseptic and dissolved therein. The solution was sterilized by filtration through a membrane filter and filled into a 20 ml container for nasal drops to give 50 compositions of the present invention each containing 0.5% diphenhydramine/20 ml.

EXAMPLE 18

Powder lyophilized in vacuo was obtained from indomethacin (2 g) and β-CyD-G$_2$-COONa (16 g) according to the same manner as that described in Example 1. According to a conventional method for producing rectal suppositories, witepsol W-35 (82 g) was melted by warming it to 55° to 60° C., and the above powder was added thereto and homogeneously dispersed with stirring well and then poured into containers for shaping 2 g suppositories and cooled slowly to shape suppositories. Thus, 50 compositions (suppositories) of the present invention containing 40 mg indomethacin per suppository were prepared.

EXAMPLE 19

According to a conventional method for producing cosmetics, microcrystalline wax (10 g), yellow bees wax (5 g), vaseline (6 g), water-containing lanolin (6 g), squalane (36 g), hexadecyladipic acid ester (8 g) and polyoxyethylene (20 mol) sorbitan monooleic acid ester (4 g) were added to a dried container, warmed to about 70° to 80° C. and stirred to give a solution (A composition). In another container, vitamin E (0.01 g) and maltosyl-β-cyclodextrincarboxylic acid (β-CyD-G$_2$-COOH) (0.1 g) were dissolved in purified water (21.4 g) at room temperature. Propylene glycol (2.5 g), perfume (0.5 g) and an appropriate amount of butyl p-hydroxybenzoate were added, warmed to about 70° C. and stirred to give a solution (B composition). Then, B composition was mixed with A composition little by litter under stirring to give an emulsion. The emulsion was degassed, filtered and cooled slowly to give 100 g facial cream, i.e., the composition of the present invention.

EXAMPLE 20

According to a conventional method for producing agricultural chemical powder, ferimzone (10 g) and maltosyl-β-cyclodextrin-carboxylic acid (β-CyD-G$_2$-COOH) (80 g) were weighed, added to purified water (200 ml), dissolved in it with stirring, and dried in vacuo to give powder. This powder was pulverized and then put through a shaking sieve to select powder having a particle size of 20 to 30μ. Thus, 80 g of powder was obtained. Separately, D-sorbit powder (20 g) having a particle size of 20 to 30 μm prepared by sieving was mixed with clay powder (100 g) in a mixer according to a conventional method. The above ferimzone /β-CyD-G$_2$-COOH powder (80 g) was added thereto, mixed well to obtain powder (200 g) of an agricultural chemical against rice blast that is the composition of the present invention.

EXAMPLE 21

Vitamin E (0.05 g) was added to an aqueous solution of maltosyl-β-cyclodextrin carboxylic acid (β-CyD-G$_2$-COOH) (0.5 g) in purified water (100 ml) and dissolved in it. The resulting solution was lyophilized in vacuo to give powder (0.55 g, after correcting the water content). According to a conventional method for producing mayonnaise foods, this powder was added to a mixing container. Further, mustard (5 g), salt (12.5 g), pepper (1.25 g), sugar (8 g) and chemical seasoning (0.75 g) were added and mixed so that grains disappear. Then, yolk (80 g) was added and mixed well using a whisk, and edible vinegar (25 g) was added and mixed well. Then, salad oil (about 15 g) was added with stirring. Further, salad oil (5 g) was added, and when the mixture became hard, edible vinegar (45 g) was added and spread. Salad oil (800 g) was added with stirring quickly. Finally, seasoning the mixture properly with edible vinegar (5 g) gave edible mayonnaise (1 kg), i.e., the composition of the present invention.

Experiment 1

Rabbit erythrocytes were added to 10 mM isotonic phosphate buffer (pH 7.4) to prepare a 0.25% suspension. To this was added sodium 6-O-cyclomaltoheptaosyl-(6→1)-α-D-glucosyl-(4→1)-O-α-D-glucuronate (β-CyD-G$_2$-COONa) so that the concentration thereof became 1 to 40 mM. The mixture was shaken at 37° C. for 30 minutes and then centrifuged to separate the supernatant. The amount of the red blood cells bursted by the action of β-CyD-G$_2$-COONa was determined by measuring the absorbance (at 543 nm) of hemoglobin in the resulting supernatant with a spectrophotometer (UV-240, Shimadzu Corp.). The amount of hemoglobin bursted in water instead of isotonic phosphate buffer was used as a standard (100%), and the relative ratio to it was indicated as a hemolytic ratio. The relationship between the hemolytic ratio and the cyclodextrin concentration is shown in FIG. 1.

Further, according to the same manner as that described above except using β-cyclodextrin (β-CyD) instead of β-CyD-G$_2$-COONa, the hemolytic ratio was determined. The results are in FIG. 1 together with the above results for comparison. As is clear from FIG. 1, β-CyD-G$_2$-COONa had much less hemolytic effect than that of β-CyD.

Experiment 2

Figure 2:
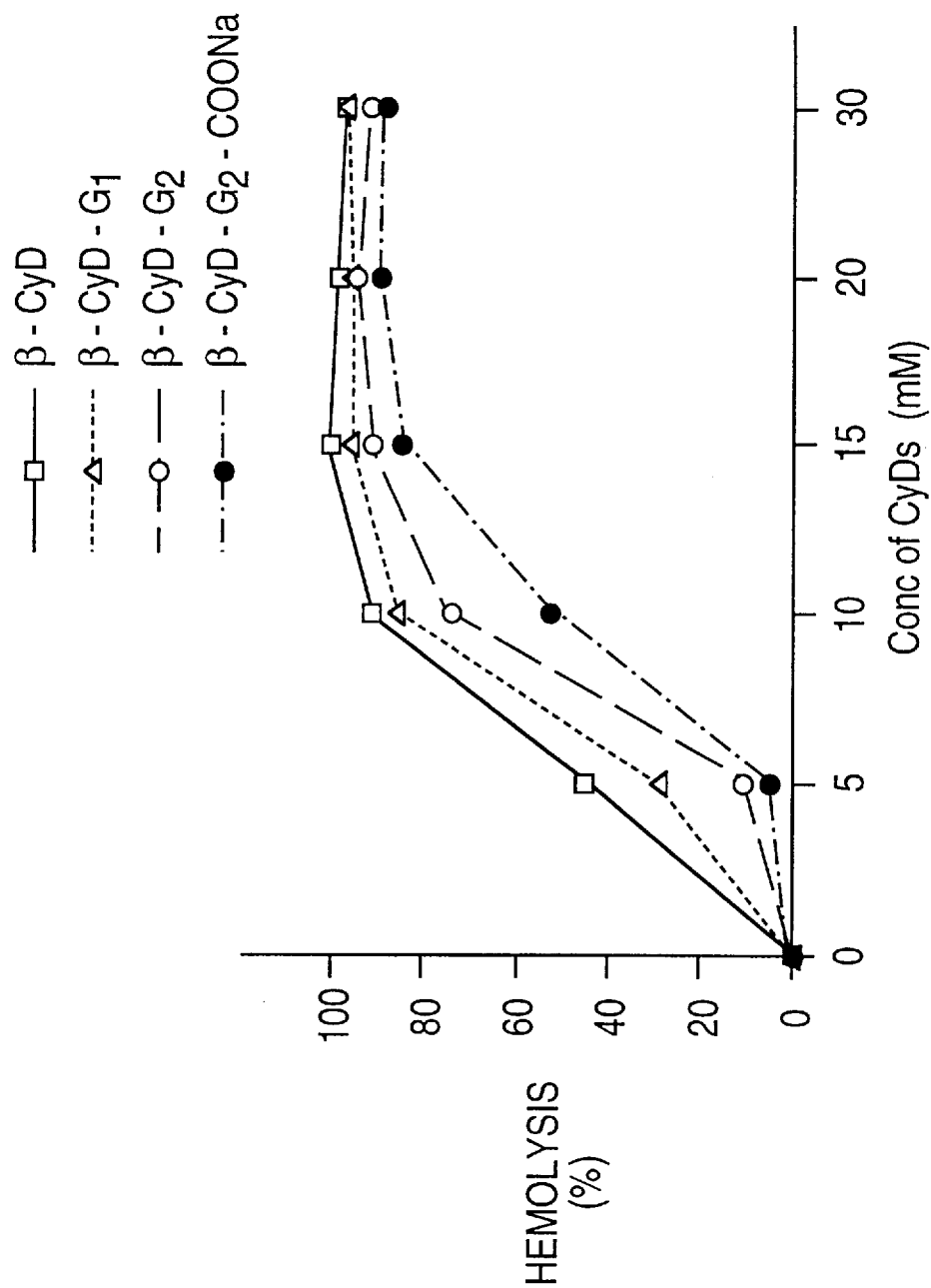
FIG. 2 is a graph showing hemolytic effects of β-CyDs on human erythrocytes in 0.1M isotonic phosphate buffer (pH 7.4) at 37° C.

Sodium 6-O-cyclomaltoheptaosyl-(6→1)-α-D-glucosyl-(4→1)-O-α-D-glucuronate (hereinafter abbreviated as β-CyD-G$_2$-COONa) was tested for its hemolytic effects to human erythrocytes. Human erythrocytes were added to 0.1M isotonic phosphate buffer (pH 7.4) to prepare a 20% suspension. The 20% erythrocyte suspension (100 μl) was added to an isotonic buffer (4 ml) containing β-CyD-G$_2$-COONa in a concentration of 5 to 30 mM. The mixture was kept at 37° C. for 30 minutes, and then centrifuged to separate the supernatant. The amount of the erythrocytes bursted by the action of β-CyD-G$_2$-COONa was determined by measuring the absorbance (at 543 nm) of hemoglobin in the resulting supernatant with a spectrophotometer (U-1080, Hitachi, Ltd., Japan). The amount of hemoglobin bursted in water instead of isotonic phosphate buffer was used as a standard (100%), and the relative ratio to it was indicated as a hemolytic ratio. The relationship between the hemolytic ratio and the cyclodextrin concentration is shown in FIG. 2.

Further, according to the same manner as that described above except using β-cyclodextrin (β-CyD), β-CyD-G$_1$ and β-CyD-G$_2$ instead of β-CyD-G$_2$-COONa, their hemolytic ratios were determined. The results are in FIG. 2 together with the above results for comparison. As is clear from FIG. 2, β-CyD-G$_2$-COONa had much less hemolytic effect than that of β-CyD, β-CyD-G$_1$ or β-CyD-G$_2$.

Experiment 3

6-O-cyclomaltoheptaosyl-(6→1)-α-D-glucosyl-(4→1)-O-α-D-glucuronic acid (β-CyD-G$_2$-COOH) was tested for its toxicity in rats. Four male rats were used. β-CyD-G$_2$-COOH was dissolved in sterilized water. The solution was intravenously administered to rats in daily doses of 1 ml/kg, 3 ml/kg, and 10 ml/kg (containing β-CyD-G$_2$-COOH in amounts of 100 mg/kg, 300 mg/kg, and 1000 mg/kg, respectively) every day for 2 weeks.

No rats died in this test. No abnormality was observed in the general appearance, diet intake amount, body weight, urine sediments, hematological examination. Pathological and histological examination revealed no serious findings such as necrosis.

As a control, the toxicity of β-CyD-G$_2$ was studied according to the same manner. Auricle flush and peripheral swelling in the extremities were observed in groups to which 300 mg/kg and 1000 mg/kg of β-CyD-G$_2$ was administered. Urine examination showed occult blood and an increase in LDH and NAG in the 1000 mg/kg β-CyD-G$_2$ administered group. Pathological and histological examination revealed renal tubule epithelium vacuolation and necrosis in the 300 mg/kg and 1000 mg/kg β-CyD-G$_2$ administered groups.

Experiment 4

The stability of 6-O-α-D-glucuronyl-(1→4)-α-D-glucosyl-β-cyclodextrin sodium salt (sodium 6-O-cyclomaltoheptaosyl-(6→1)-α-D-glucosyl-(4→1)-O-α-D-glucuronate) (β-CyD-G$_2$-COONa) to various enzymes was tested by the following method. As a control, 6-O-α-maltosyl-β-cyclodextrin was used.

Test method:

Each of prescribed amounts of the following enzymes was added to a 10 mM aqueous solution of cyclodextrin to be tested. The mixture was allowed to stand in a water bath at 37° C. 50 μl of each mixture was sampled, and the enzyme was inactivated by heating it at 100° C. for 15 minutes, centrifuged at 15,000 rpm for 5 minutes, filtered through Millipore USY-1 (differential molecular weight: 10,000), diluted 10 times and subjected to HPLC analysis.

HPLC analytic conditions:
Column; NH2P-50 (Asahipak)
Mobile phase; CH$_3$CN:H$_2$O=48:52 to which 0.005M PIC reagent was added.
Flow rate; 0.8 ml/minute
Detection; RI The ratio of the remaining cyclodextrin at 0 to 120 minutes was determined from the above HPLC analysis of each sample.

The relationship between the enzyme used and the enzyme concentration is shown in Table 16.

TABLE 16

The enzymes and the concentration of the enzyme used

| Enzyme | Origin | Concentration of enzyme used (unit/ml) |
|---|---|---|
| α-Amylase | Bacillus subtilis (manufactured by Wako Pure Chemical) | 20 |
| Glucoamylase | Rhizopus sp. (manufactured by Wako Pure Chemical) | 2 |
| Pullulanase | Klebsiella pneumoniae (manufactured by Hayashibara) | 10 |
| βGlucuronidase | Calf liver (manufactured by Wako Pure Chemical) | 700 |

Each unit is as described in the instruction book of the enzyme obtained from the above supplier, Results:

Changes of the ratio of remaining 6-O-α-D-glucuronyl (1→4)-α-D-glucosyl-β-cyclodextrin sodium salt (branched cyclodextrin-carboxylic acid salt) and 6-O-α-maltosyl-β-cyclodextrin (branched cyclodextrin) with the passage of time are shown in FIGS. 3 to 6. In the figures, black triangles represent the branched cyclodextrin-carboxylic acid salt, and black dots represent the branched cyclodextrin.

Figure 3:
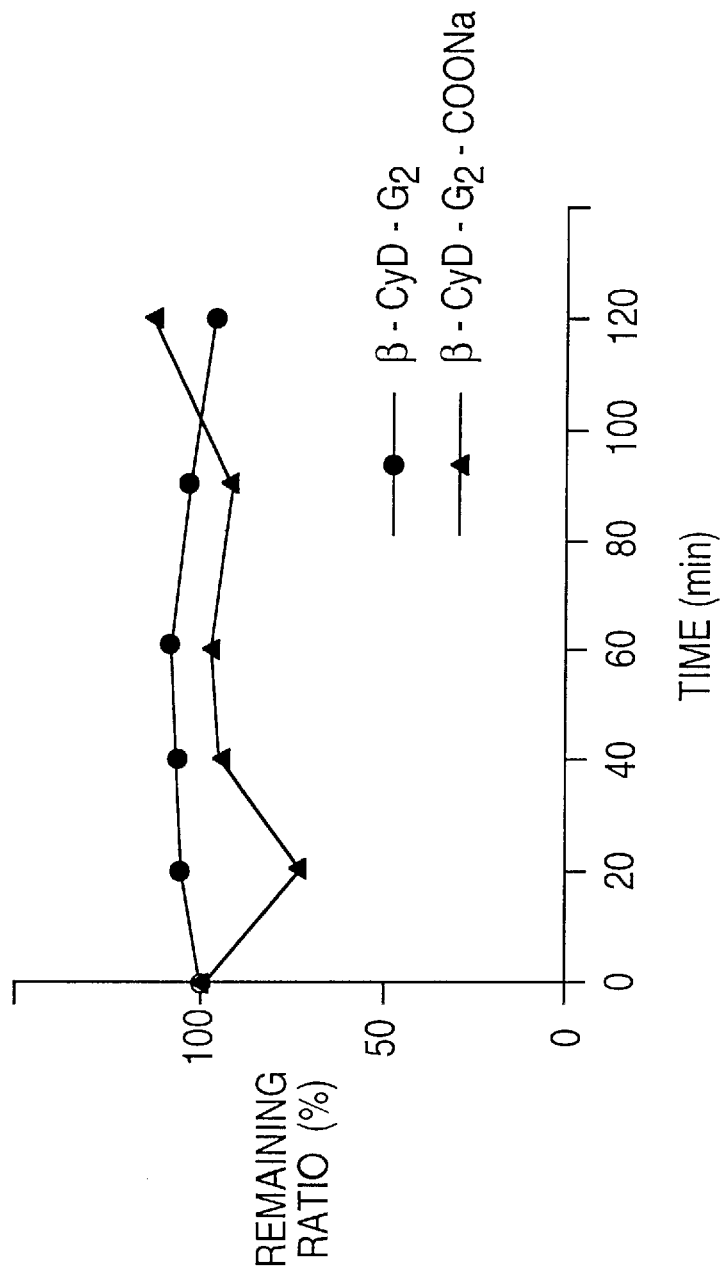
FIG. 3 is a graph showing the stabilities of a branched cyclodextrin-carboxylic acid salt and a branched cyclodextrin to α-amylase.
Figure 4:
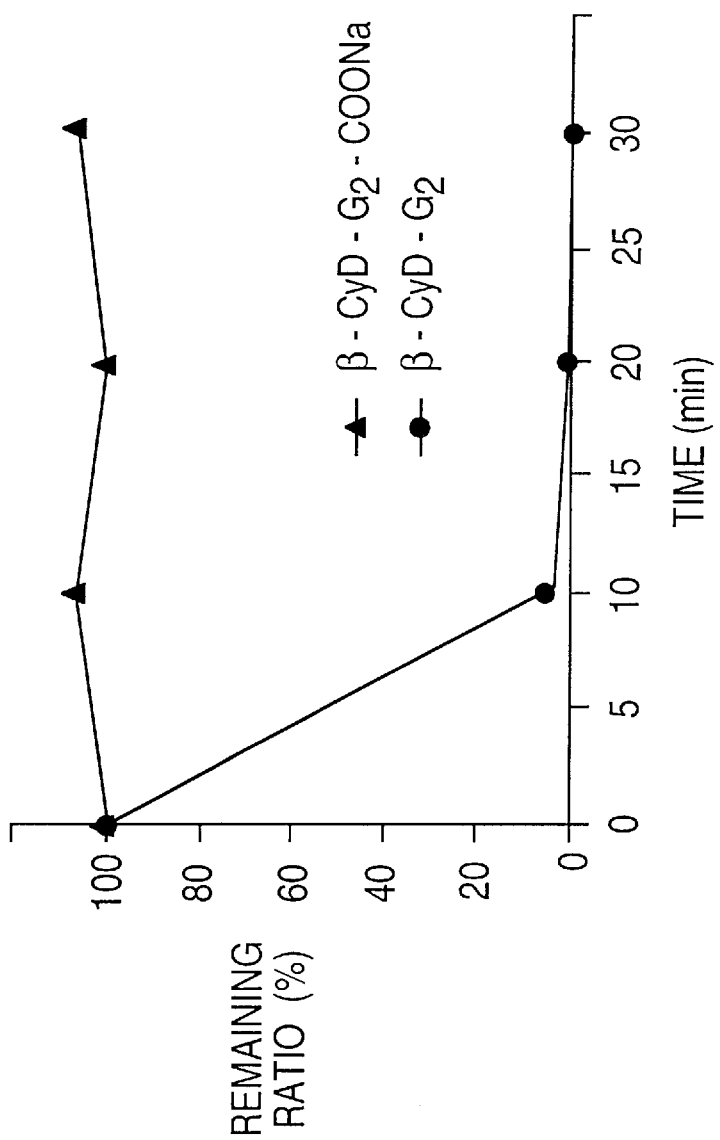
FIG. 4 is a graph showing the stabilities of a branched cyclodextrin-carboxylic acid salt and a branched cyclodextrin to glucoamylase.
Figure 5:
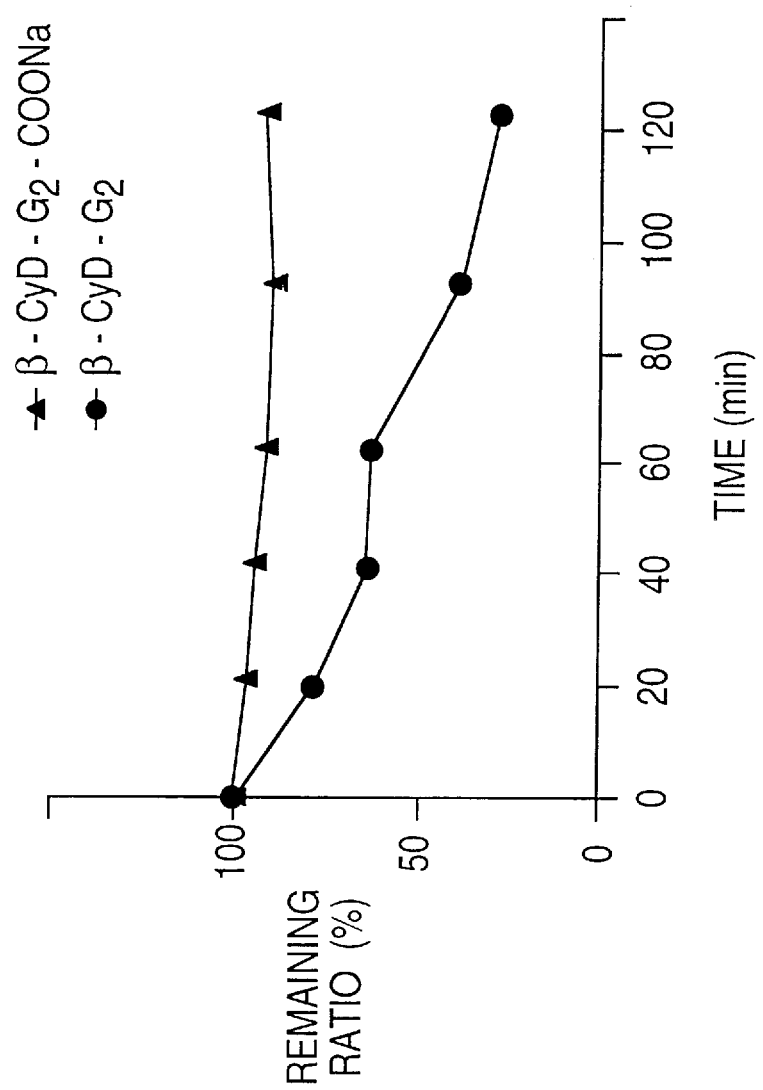
FIG. 5 is a graph showing the stabilities of a branched cyclodextrin-carboxylic acid salt and a branched cyclodextrin to pullulanase.
Figure 6:
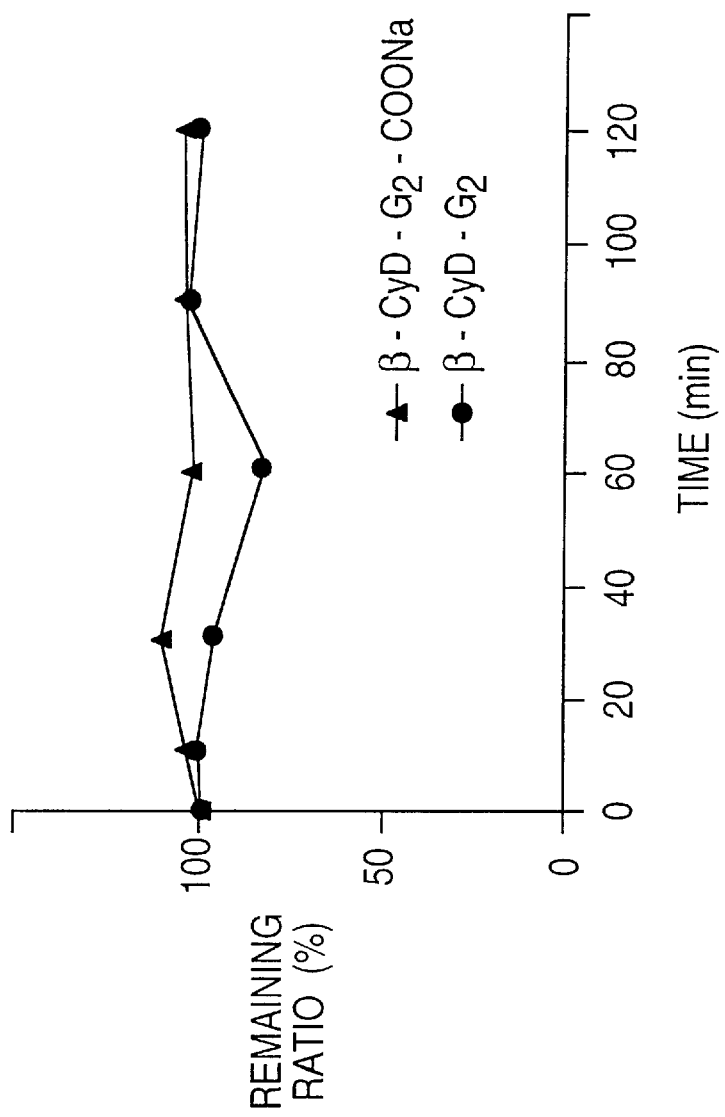
FIG. 6 is a graph showing the stabilities of a branched cyclodextrin-carboxylic acid salt and a branched cyclodextrin to β-glucuronidase.

FIGS. 4 to 6 clearly show that the branched cyclodextrin-carboxylic acid salt is more stable to the enzymatic treatments with glucoamylase, pullulanase and β-glucuronidase than 6-O-α-maltosyl-β-cyclodextrin as a control. The two β-cyclodextrins had almost the same stabilities to the enzymatic treatment with α-amylase, as shown in FIG. 3.

Especially, in the study on the enzymatic treatment with pullulanase, about 60% of 6-O-α-maltosyl-β-cyclodextrin as a control decomposed, while the branched cyclodextrin-carboxylic acid salt was stable.

Experiment 5

According to the same manner as that described in Example 1, an aqueous solution of β-CyD-G$_2$-COONa was added to a solution (25 μl) of the anticancer agent taxol (125 μg) in methanol so that the molar ratio of β-CyD-G$_2$-COONa to taxol became 1:2, 1:10 and 1:20. The mixture was stirred at 30° C. for 24 hours. Water was added to the reaction mixture to a total volume of 5 ml and filtered through a Millipore filter with a pore size of 0.2 μm. The filtrate was lyophilized to give colorless powder.

This powder was dissolved in water, and the amount of taxol in 1 mg of the lyophilized powder was determined by HPLC.

HPLC conditions:

Column: μ Bondapack C$_{18}$ (3.9 mm×15 cm)
Mobile phase: MeOH:H$_2$O=3:2
Flow rate: 0.7 ml/minute
Detection: UV 230 nm
Injected amount: 10 μl
Taxol: Rt=12.3

Results:

Lyophilized powder prepared in a molar ratio of 1:10 2.09 μg/ml

Lyophilized powder prepared in a molar ratio of 1:20 1.85 μg/ml

The results show that addition of β-CyD-G$_2$-COONa in a molar ratio of 1:10 to 1:20 solubilize taxol.

Reference Example 1

Maltosyl-β-cyclodextrin (30 g) was added to a cell suspension (1 liter) of *Pseudogluconobacter saccharoketogenes* TH14-86 (as prepared in Reference Example 2) and reacted at 32° C. and 800 rpm for 1 hour with aerating at 1.6 liter air/minute. Then, this reaction mixture was subjected to a cool centrifuge at 8000 rpm to remove the cells. The supernatant was passed through HP-20 column (1.5 L) and washed with water (2 L). The fractions eluted with 20% aqueous methanol solution were combined, concentrated and lyophilized to give 6-O-[α-D-glucuronyl-(1→4)-α-D-glucosyl]-β-cyclodextrin sodium salt (β-CyD-G$_2$-COONa) (25 g). The physical and chemical data of this compound are as follows.

Compound: 6-O-α-D-glucuronyl-(1→4)-α-D-glucosyl-β-cyclodextrin Na salt (also referred to as 6-O-cyclomaltoheptaosyl-( 6→1)-D-α-glucosyl-(4→1)-O-α-D-glucuronic acid Na salt)

(starting material: 6-O-α-maltosyl-β-cyclodextrin)

$^{13}$C-NMR: Na salt: D$_2$O (270 MHz) δppm: 61.69, 61.89, 68.54, 71.84, 72.16, 72.47, 73.14, 73.21, 73.30, 73.49, 73.57, 74.23, 74.33, 74.50, 74.71, 79.62, 82.52, 82.57, 82.74, 83.02, 100.01, 101.58, 103.25, 103.31, 103.37, 177.84

Elemental Analysis: Calcd. for C$_{54}$H$_{87}$O$_{46}$Na.10H$_2$O: C,38.71; H,6.43 Found: C,38.87; H,6.47 mp: >260° C. (decomposition)

$[α]_D^{20}$=+146.9° (c=0.61% water)

Solubility: >200 g/100 ml (25° C., H$_2$O) (Control: 6-O-α-D-glucosyl-(1→4)-α-D-glucosyl-β-cyclodextrin 150 g/100 ml (25° C., H$_2$O))

Half-life in 0.1N HCl solution at 60° C.: 8 hr (Control: 6-O-α-D-glucosyl-(1→4)-α-D-glucosyl-β-cyclodextrin 5 hr)

Hemolysis: The concentration hemolyzing 50% of the rabbit red cells in phosphate buffer (pH 7.4) at 37° C. was 11 mM.

(Control: β-cylodextrin 4 mM, 6-O-α-D-glucosyl-(1→4)-α-D-glucosyl-β-cyclodextrin 8 mM)

According to the same manner as that described above, 6-O-(2-carboxyethyl)-β-cyclodextrin sodium salt, 6,6 -di-O-(2-carboxyethyl)-β-cyclodextrin, 6-O-α-D-glucuronyl-(1→4)-α-D-glucosyl-α-cyclodextrin/sodium salt, 6-O-(α-D-glucuronyl)-β-cyclodextrin, 6-O-[α-D-glucuronyl-(1→4)-α-D-glucosyl]-α-cyclodextrin, 6-O-(2-carboxy-2-hydroxyethyl)-β-cyclodextrin sodium salt, 6,6'-di-O-(2-carboxyethyl-2-hydroxyethyl)-β-cyclodextrin sodium salt were prepared. Their physical and chemical data are as follows.

Compound: 6-O-(2-carboxyethyl)-β-cyclodextrin Na salt and 6,6-di-O-(2-carboxyethyl)-β-cyclodextrin Na salt (also referred to as 3-O-(6-cyclomaltoheptaosyl)propionic acid Na salt)

(starting compounds: 6-O-(3-hydroxypropyl)-β-cyclodextrin and 6,6-di-O-(3-hydroxypropyl)-β-cyclodextrin, respectively)

$^{13}$C-NMR: Na salt: D$_2$O (270 MHz) δppm: Carbon signals based on the carboxylic acid were observed at 181.127, 181.508 and 185.076 ppm.

Compound: 6-O-α-D-glucuronyl-(1→4)-α-D-glucosyl-α-cyclodextrin Na salt (also referred to as 6-O-cyclomaltohexaosyl-(6→1)-D-α-glucosyl-(4→1)-O-α-D-glucuronic acid Na salt)

(starting compound: 6-O-α-maltosyl-α-cyclodextrin)

$^{13}$C-NMR: Na salt: D2O (270 MHz) δppm: A carbon signal based on the carboxylic acid was observed at 177.105 ppm.

Compound: 6-O-α-D-glucuronyl-β-cyclodextrin (also referred to as 6-O-cyclomaltoheptaosyl-(6→1)-α-D-glucuronic acid)

(starting compound: 6-O-α-D-glucosyl-β-cyclodextrin)

TLC:

Silica gel: Merck Kiesel Gel 60 (F$_{254}$ No. 5715)

Eluent: 1-propanol: ethyl acetate: water: acetic acid (6:4:2:4)

Yield: 64%

Rf=0.25

$^{13}$C-NMR (270 MHz, D$_2$O) δppm: A carbon signal based on the carboxylic acid was observed at 178.070 ppm.

Compound: 6-O-[α-D-glucuronyl-(1-4)-α-D-glucosyl]-α-cyclodextrin (also referred to as 6-O-cyclomaltohexaosyl-(6→1)-α-D-glucosyl-(4→1)-O-α-D-glucuronic acid)

(starting compound: 6-O-maltosyl-α-cyclodextrin)

HPLC: Column NH2P-50

Mobile phase: Acetonitrile:Water=55:45,

Flow rate: 1 ml/min,

Yield: 68%

Temperature: 25° C.

RT=7.58

Compound: 6-O-(2-carboxy-2-hydroxyethyl)-β-cyclodextrin Na salt (also referred to as 2-hydroxy-3-O-(6-cyclomaltoheptaosyl)-propionic acid Na salt) and 6,6-di-O-(2-carboxy-2 -hydroxyethyl)-β-cyclodextrin Na salt (also referred to as 7$^A$, 7$^C$-di-O-[α-D-glucuronyl-(1→4)-O-α-D-glucosyl]-(1→6)-maltoheptaose Na salt)

(starting compounds: 6-O-(2,3-dihydroxypropyl)-β-cyclodextrin and 6,6'-di-O-[(2,3-dihydroxypropyl)]-β-cyclodextrin, respectively)

$^{13}$C-NMR (270 MHz, D$_2$O) δppm: 177.762, 177.883, and 180.068.

Compound: 6-O-cyclomaltohexaosyl-(6→1)-α-D-glucuronic acid (α-CyD-G$_1$-COOH)

$^{13}$C-NMR (270 MHz, D$_2$O) δppm: 179.611 (COOH).

$[α]_D$=+125.4° (c=0.956, H$_2$O)

Compound: 6-O-cyclomaltooctaosyl-α-D-glucosyl-(4→1)-O-α-D-glucuronic acid (γ-CyD-G$_2$-COOH)

$^{13}$C-NMR (270 MHz, D$_2$O) δppm: 179.116 (COOH).

$[α]_D$=+155.90 (c=1.035, H$_2$O)

Compound: Calcium 6-O-cyclomaltoheptaosyl-O-α-D-maltosyl-(4→1)-O-α-D-glucuronate (also named as calcium cyclomaltoheptaosyl-(6→1)-O-α-D-glucopyranosyl-(4→1)-O-α-D-glucopyranosyl-(4→1)-O-α-D-glucopyranoiduronate) (β-CyD-G$_3$-COOCa)

HPLC: Column NH2P-50

RT=20.70 (min)

Sample size: 10 mg/ml

Eluent: Acetonitrile-Water (48:52)+PICA reagent

Flow rate: 0.8 ml/min

Temperature: 25° C.

Detector: RI

Reference Example 2

One loopful of *Pseudogluconobacter saccharoketogenes* TH14-86 was transferred from a slant culture to a 200 ml smooth-walled flask containing the medium (20 ml) described below and precultured on a rotary shaker at 30° C. for 1 day. Then, 1 ml of the culture per 20 ml medium was shake-cultured at 30° C. for 20 days to prepare a seed culture. Also, 1 loopful of *Bacillus megaterium* IFO 12108 was transferred from a slant culture to a 200 ml smooth-walled flask containing the medium (20 ml) described below and shake-cultured at 30° C. for 2 days.

Jar fermentation was then carried out under the following conditions. Thus, 100 ml of the above seed culture (seed medium) of TH14-86 and 1.5 ml of the seed medium of *Bacillus megaterium* were added to the main culture medium described below and shake culture was carried out at 30° C. for about 20 hours to provide a cell suspension of *Pseudogluconobacter saccharoketogenes* TH14-86.

| (Medium compositions) | |
|---|---|
| [Seed medium for TH14-86] (in common for 1st and 2nd cultures) | |
| Lactose | 1% |
| Yeast extract (Prodivel) | 1% |
| $(NH_4)_2SO_4$ | 0.3% |
| Corn steep liquor | 3% |
| $CaCO_3$ (Super) | 2% |
| pH before addition of $CaCO_3$ = 7.0 | |
| [Seed medium for *Bacillus megaterium*] | |
| Sucrose | 4% |
| Proflo [N source, Tradas Protein (T & P) ] | 4% |
| $K_2HPO_4$ | 0.65% |
| $KH_2PO_4$ | 0.55% |
| NaCl | 0.05% |
| $(NH_4)_2SO_4$ | 0.05% |
| $MgSO_4.7H_2O$ | 0.005% |
| Calcium pantothenate | 0.025% |
| pH before sterilization = 7.0 | |
| [Main medium] | |
| Sucrose | 0.05%, independently sterilized |
| Corn steep liquor independently sterilized | 2%, |
| $(NH_4)_2SO_4$ | 0.3%, independently sterilized |
| $FeSO_4.7H_2O$ | 0.1%, independently sterilized |
| Vitamin $B_2$ | 1 mg/l, |
| pH before sterilization = 7.0 | |
| Sorbose | 10%, independently sterilized |
| $LaCl_3$ | 0.01%, independently sterilized |
| $CaCO_3$ (Super) | 4%, independently sterilized |

What is claimed is:

1. A composition comprising a water-insoluble or slightly water-soluble compound and a branched cyclodextrin-carboxylic acid, said branched cyclodextrin-carboxylic acid being selected from the group consisting of 6-O-cyclomaltoheptaosyl-(6→1)-α-D-glucosyl-(4→1)-O-α-D-glucuronic acid, 6-O-cyclomaltoheptaosyl-(6→1)-α-D-glucuronic acid and 2-hydroxy-3-O-(6-cyclomaltoheptaosyl)propionic acid.

2. A composition according to claim 1, wherein the branched cyclodextrin-carboxylic acid is 6-O-cyclomaltoheptaosyl-(6→1)-α-D-glucosyl-(4→1)-O-α-D-glucuronic acid.

3. A composition according to claim 1, wherein the branched cyclodextrin-carboxylic acid is 6-O-cyclomaltoheptaosyl- (6→1)-α-D-glucuronic acid.

4. A composition comprising a water-insoluble or slightly water-soluble compound having a water solubility of not more than 10 mg/ml and a branched cyclodextrin-carboxylic acid, said branched cyclodextrin-carboxylic acid having as the branched moiety, (1) a group containing 1 to 3 glucosyl groups such that at least one hydroxymethyl group of the glucosyl groups in the branched moiety has been oxidized to a carboxyl group or (2) 2-carboxy-2-hydroxyethyl, at the 6-O-position of at least one glucose unit of the cyclodextrin ring.

5. A composition comprising a water-insoluble or slightly water-soluble compound and a branched cyclodextrin-carboxylic acid which is produced microbiologically, said branched cyclodextrin-carboxylic acid having as the branched moiety, (1) a group containing 1 to 3 glucosyl groups such that at least one hydroxymethyl group of the glucosyl groups in the branched moiety has been oxidized to a carboxyl group or (2) 2-carboxy-2-hydroxyethyl, at the 6-O-position of at least one glucose unit of the cyclodextrin ring.

6. A composition according to claim 5, wherein the branched cyclodextrin-carboxylic acid is produced by microbiological selective oxidation using a microorganism belonging to the genus Pseudogluconobacter.

* * * * *